US010792086B2

(12) United States Patent
Trivedi et al.

(10) Patent No.: US 10,792,086 B2
(45) Date of Patent: *Oct. 6, 2020

(54) CAUTERY APPARATUS (71) Applicant: Covidien LP, Mansfield, MA (US)

(72) Inventors: Amit Trivedi, Upper Saddle River, NJ (US); Thomas J. Campanelli, Berlin, CT (US); Roberto Pedros, Oxford, CT (US)

(73) Assignee: COVIDIEN LP, Mansfield, MA (US)

( * ) Notice: Subject to any disclaimer, the term of this patent is extended or adjusted under 35 U.S.C. 154(b) by 1017 days.

This patent is subject to a terminal disclaimer.

(21) Appl. No.: 14/955,962

(22) Filed: Dec. 1, 2015

(65) Prior Publication Data

US 2016/0128757 A1    May 12, 2016

Related U.S. Application Data (63) Continuation-in-part of application No. 14/615,763, filed on Feb. 6, 2015, now Pat. No. 10,278,759.

(60) Provisional application No. 62/075,897, filed on Nov. 6, 2014.

(51) Int. Cl.
*A61B 18/08* (2006.01)
*A61B 18/00* (2006.01)

(52) U.S. Cl.
CPC .. *A61B 18/082* (2013.01); *A61B 2018/00589* (2013.01); *A61B 2018/00595* (2013.01); *A61B 2018/00922* (2013.01); *A61B 2018/00958* (2013.01); *A61B 2218/005* (2013.01)

(58) Field of Classification Search
CPC .......... A61B 2018/00922; A61B 2018/00958; A61B 2018/048; A61B 2018/0094
See application file for complete search history.

(56) References Cited

U.S. PATENT DOCUMENTS

| | | |
|---|---|---|
| 2,708,933 A | 5/1955 | August |
| 2,808,833 A | 10/1957 | August |
| 2,828,748 A | 4/1958 | August |
| 3,991,764 A | 11/1976 | Incropera et al. |

(Continued)

OTHER PUBLICATIONS

U.S. Appl. No. 62/075,897, filed Nov. 6, 2014, Amit Triveti.
Extended European Search Report issued in corresponding Appl. No. 16871465.7 dated Aug. 16, 2019 (8 pages).

*Primary Examiner* — Linda C Dvorak
*Assistant Examiner* — Ryan T Clark (57) ABSTRACT A cautery device includes an elongated handpiece extending axially from a proximal end to a distal end and a cautery tip extending coaxially with the handpiece from the distal end of the handpiece. The tip defines a channel extending coaxially with the handpiece along at least a portion of the length of the cautery tip from a proximal open end to a distal end. The device includes a gas supply connection extending from the proximal end of the handpiece for supplying gas to the cautery tip. The gas supply connection is fluidly coupled to the cautery tip. The device includes an electric supply connection extending from the proximal end of the handpiece for supplying electricity to the cautery tip. The electric supply connection is electrically coupled to the cautery tip. The gas supplied to the cautery tip is introduced to the channel at the proximal open end and exits to envelop the distal tip.

20 Claims, 9 Drawing Sheets (56) References Cited

U.S. PATENT DOCUMENTS

| | | | |
|---|---|---|---|
| 4,274,070 A * | 6/1981 | Thiene | H01H 9/06 335/205 |
| 4,562,838 A | 1/1986 | Walker | |
| 4,781,175 A | 11/1988 | McGreevy et al. | |
| 5,098,430 A | 3/1992 | Fleenor | |
| 5,217,457 A | 6/1993 | Delhuerga et al. | |
| 5,256,138 A | 10/1993 | Burek et al. | |
| 5,306,238 A | 4/1994 | Fleenor | |
| 5,312,400 A | 5/1994 | Bales et al. | |
| 5,344,548 A | 9/1994 | Alberti et al. | |
| 5,376,089 A | 12/1994 | Smith | |
| 5,480,397 A | 1/1996 | Eggers et al. | |
| 5,541,376 A | 7/1996 | Ladtkow et al. | |
| 5,593,406 A | 1/1997 | Eggers et al. | |
| 5,702,387 A | 12/1997 | Arts et al. | |
| 5,720,745 A | 2/1998 | Farin et al. | |
| 5,951,548 A | 9/1999 | DeSisto et al. | |
| 6,076,392 A | 6/2000 | Drzewiecki | |
| 6,197,026 B1 | 3/2001 | Farin et al. | |
| 6,250,132 B1 | 6/2001 | Drzewiecki | |
| 6,266,995 B1 | 7/2001 | Scott | |
| 6,272,905 B1 | 8/2001 | Drzewiecki | |
| 6,305,212 B1 | 10/2001 | Drzewiecki | |
| 6,348,051 B1 | 2/2002 | Farin et al. | |
| 6,458,125 B1 | 10/2002 | Cosmescu | |
| 6,723,091 B2 | 4/2004 | Goble et al. | |
| 6,747,218 B2 | 6/2004 | Huseman et al. | |
| 6,958,063 B1 | 10/2005 | Soll et al. | |
| 7,150,747 B1 | 12/2006 | McDonald et al. | |
| 7,296,571 B2 | 11/2007 | Foltz et al. | |
| 7,303,559 B2 | 12/2007 | Peng et al. | |
| 7,537,594 B2 | 5/2009 | Sartor | |
| 7,585,295 B2 | 9/2009 | Ben-Nun | |
| 8,241,278 B2 | 8/2012 | Sartor | |
| 2003/0052792 A1 | 3/2003 | Koyano et al. | |
| 2004/0034339 A1 | 2/2004 | Stoller et al. | |
| 2004/0129270 A1 | 7/2004 | Fishman | |
| 2004/0138658 A1 | 7/2004 | Farin et al. | |
| 2004/0167512 A1 | 8/2004 | Stoddard et al. | |
| 2004/0181220 A1 | 9/2004 | Farin | |
| 2005/0015086 A1 | 1/2005 | Platt | |
| 2005/0021021 A1 | 1/2005 | Foltz et al. | |
| 2005/0187537 A1 | 8/2005 | Loeb et al. | |
| 2006/0036239 A1 | 2/2006 | Canady | |
| 2006/0052774 A1 | 3/2006 | Garrison et al. | |
| 2006/0069387 A1 | 3/2006 | Gedebou | |
| 2006/0178667 A1 | 8/2006 | Sartor et al. | |
| 2009/0076505 A1 * | 3/2009 | Arts | A61B 18/042 606/49 |
| 2014/0276717 A1 * | 9/2014 | Wan | A61B 18/042 606/29 |
| 2014/0276758 A1 * | 9/2014 | Lawrence | A61B 18/1492 606/33 |
| 2015/0088114 A1 | 3/2015 | Stringham et al. | |
| 2016/0128756 A1 | 5/2016 | Trivedi | |

* cited by examiner

CAUTERY APPARATUS

CROSS REFERENCE TO RELATED APPLICATIONS

This application is a continuation-in-part of U.S. Ser. No. 14/615,763, filed Feb. 6, 2015, which claims the benefit of priority under 35 U.S.C. § 119(e) to provisional application 62/075,897, filed on Nov. 6, 2014, the entire contents of which are incorporated herein by reference in their entireties.

BACKGROUND

1. Field

The present invention relates to surgical instruments, and more particularly a cautery apparatus.

2. State of the Art

Cautery devices have been used in surgical procedures to perform cutting and coagulation of tissue and blood vessels. Typically, cautery devices are "pen"-like devices that a surgeon can grasp by the hand to use. The cautery device typically is connected to an electrical generator that outputs a level of current that is conducted to a tip of the device to achieve the desired cutting and/or coagulation effect during a surgical procedure.

The use of cautery devices on tissue results in the generation of smoke and vapor, which are unwanted byproducts that reduce visibility in the area of the tip. Also, cautery devices have the potential to provide enough energy to cause fires in an operating room environment, which is typically a high oxygen environment. Approximately 500 operating room fires occur in the United States each year, the vast majority of which are related to a cautery device.

SUMMARY

According to a first aspect, a cautery device includes an elongated handpiece extending axially from a proximal end to a distal end and a cautery tip extending coaxially with the handpiece from the distal end of the handpiece. The tip defines a coaxial channel extending from the handpiece and along an entire length of the cautery tip from a proximal open end to a distal open end. The device includes a gas supply connection extending from the proximal end of the handpiece for supplying gas to the cautery tip. The gas supply connection is fluidly coupled to the cautery tip. The device includes an electric supply connection extending from the proximal end of the handpiece for supplying electricity to the cautery tip. The electric supply connection is electrically coupled to the cautery tip. The gas supplied to the cautery tip is introduced to the channel at the proximal open end and exits the tip at the distal open end.

According to a second aspect, the cautery device includes a multilumen tube extending from the proximal end of the handpiece. The tube defines a gas lumen extending along substantially the entire length of the tube and defining at least one electrical conductor lumen coextensive with the gas lumen. The gas lumen is in fluid communication with the cautery tip and supplies gas to the cautery tip. The gas supplied to the cautery tip is introduced to the channel at the proximal open end and exits the tip at the distal open end. The device also includes at least one electrical conductor extending through the at least one electrical conductor lumen. The electrical conductor is electrically coupled to the cautery tip for supplying electricity to the cautery tip.

According to a third aspect, the cautery device includes a switch configured to regulate the supply of electric power to the cautery tip based on the position of the handpiece relative to a holder that is constructed to receive the handpiece.

BRIEF DESCRIPTION OF THE DRAWINGS

FIG. 3 shows a view of the cautery device of FIG. 1a along section 3-3 in FIG. 1a.

FIG. 4 shows a view of a portion of the cautery device along section 4-4 in FIG. 3.

FIG. 5a shows the cautery device of FIG. 1a configured with an integrated multilumen gas and electrical conductor arrangement.

FIG. 5b shows the multilayer tubing of FIG. 5a along section 5b-5b in FIG. 5a.

DETAILED DESCRIPTION

Figure 1A:
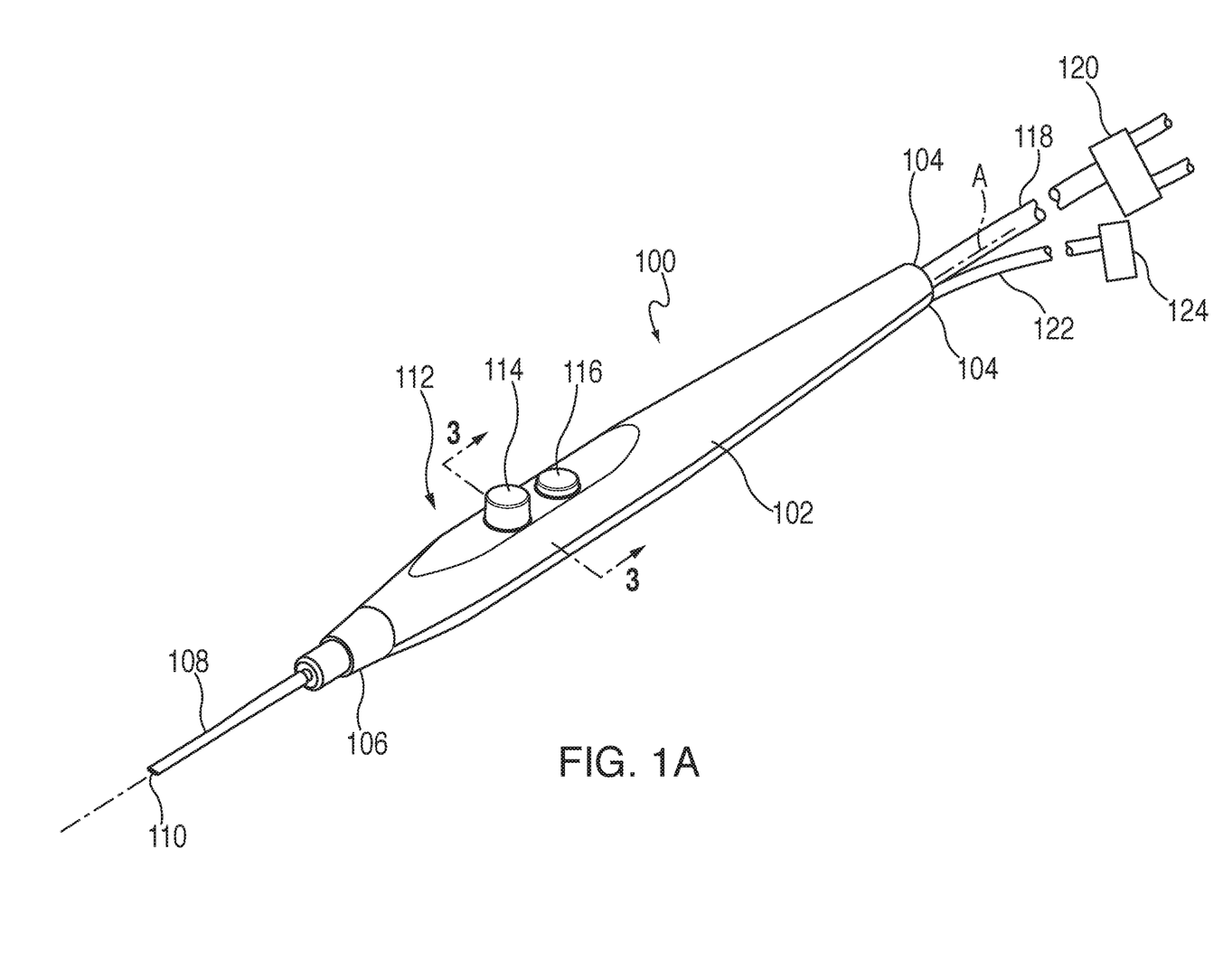
FIG. 1a is an isometric view of an embodiment of a cautery device.

FIG. 1A shows an embodiment of a cautery device 100 that includes an elongated housing 102 that extends longitudinally along an axis A-A from a proximal end 104 to a distal end 106. The device 100 also includes a removable hollow cautery tip 108 that extends longitudinally from the housing coaxially with axis A-A. The cautery tip 108 defines an open channel 110 that extends axially completely through the tip 108. The open channel 110 is preferably coaxial with the axis A-A. The housing 102 defines a handpiece 112 that is arranged so that it may be grasped in a user's hand like a writing instrument to direct the cautery tip 108 during a surgical procedure while also allowing a user of the device 100 to actuate buttons 114, 116 that extend from the housing 102. As will be described in greater detail below, the cautery tip 108 receives electric power to operate the tip 108 so that it can be used to perform various cautery tool procedures, such as cutting and coagulation. Also, the cautery device 100 is constructed to selectively permit gas to flow through the open channel 110 of the cautery tip 108.

The cautery device 100 is operated in various modes in response to selective actuation of one or more of the buttons 114, 116, as will be described in greater detail below. Each of the buttons 114, 116 may operate the cautery device 100 in a corresponding mode of operation, such as a coagulation mode and a cutting mode. Also, one or more of the buttons 114, 116 may be a multi-function button. For example, each respective button 114, 116 may be arranged to both control a gas flow of a gas through the cautery tip 108, as well as control power output to the cautery tip 108 based on the mode of operation corresponding to each button 114, 116. More specifically, in one embodiment, a first button 114 may correspond to the cutting mode and a second button 116 may correspond to the coagulation mode. In such an embodiment, selectively actuating the first button 114 may set a first gas flow rate through the cautery tip 108 and a power level corresponding to the cutting mode, while selectively actuating the second button 116 may set a second gas flow rate to the cautery tip 108 and a power level corresponding to the coagulation mode. Thus, a user of the device 100 may select the operating mode of the device by selecting and pressing a corresponding button 114, 116.

A power cord 118 and a gas tube 122 extend from the proximal end 104 of the cautery device 100. The power cord 118 supplies electric power to the device 100 from an electric power supply 120. The gas tube 122 supplies a gas to the device 100 from a source of pressurized gas 124. The gas may be an inert gas such as carbon dioxide or nitrogen. Preferably, the gas is heavier than oxygen to drive away oxygen from the area proximate to the cautery tip 108 so that the gas issuing from the cautery tip 108 can create a non-flammable zone around the tip 108.

Figure 1B:
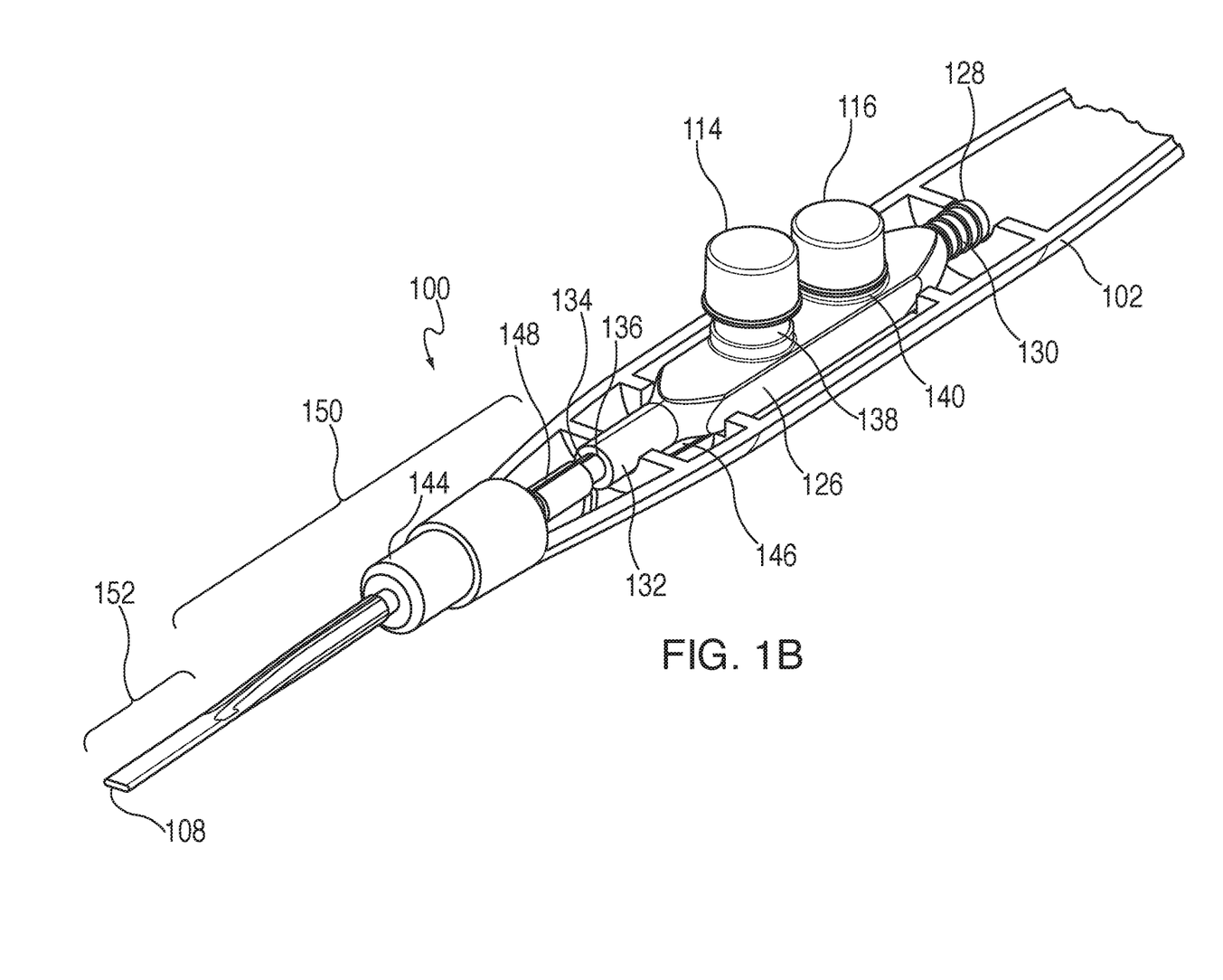
FIG. 1b is a detailed cutaway section view of the cautery device of FIG. 1a with a portion of a housing removed for purposes of illustration.

FIG. 1B shows the cautery device 100 with a portion of the housing 102 removed for purpose of illustrating some housed elements of the device 100. The device 100 includes a valve train 126 coupled to the buttons 114, 116. The valve train 126 has a proximal end 128 that is formed as a barbed male coupler 130 for coupling to a distal end of the tubing 122 (FIG. 1A). The valve train 126 also has a distal end 132 that may be formed as a female quick-connect tube coupler 134 for removably coupling to a proximal end 136 of the cautery tip 108.

In the embodiment shown in FIG. 1B, the valve train 126 includes a first valve 138 that may be actuated by the first button 114 and includes a second valve 140 that may be actuated by the second button 116. In one embodiment the valves 138, 140 are biased so that they are normally-closed valves such that the user must depress the respective button to open the valves 138, 140. When the cautery tip 108 is fluidly coupled to the valve train 126, the valve train 126 controls the flow of pressurized gas through the tip assembly by operation of the valves 138, 140, which are actuated using the buttons 114, 116.

The cautery tip 108 is removably coupled in a collet 144 that is provided at the distal end of the handpiece 112. The cautery tip 108 extends through the collet 144. More specifically, when the cautery tip 108 is fully coupled to the handpiece 112, as shown in FIG. 1B, the cautery tip 108 is fluidly coupled to the valve train 126 and is electrically coupled to an electrical unit 146 (shown partially concealed beneath the valve train 126 in FIG. 1B) via an electrical coupler or socket 148, as will be described in greater detail below.

In the embodiment shown in FIGS. 1A and 1B, the cautery tip 108 has a generally cylindrical, proximal portion 150 that extends through the collet 144 and to the fluid and electrical couplers 134, 148. The cautery tip 108 also has a flattened distal portion 152. The cylindrical proximal portion 150 tapers to the flattened distal portion 152 distally of the collet 144. The cautery tip 108 is formed of a metal that is coated with a conductive polymer. A silicone cover may also be applied to a portion of the tip 108 between the flattened portion 152 and the collet 144. The flattened distal portion 152 has a generally rectangular cross-sectional profile. It will be appreciated, however, that the cautery tip 108 may have other profiles than that shown in FIG. 1B. The cautery tip 108 is removably coupled to the handpiece 112 to facilitate tip replacement and interchanging different cautery tips (e.g., with different forms) with the same handpiece 112. To provide such interchangeability, the electrical and fluid couplers 148 and 134 may be constructed as removable couplers, such as a fluid quick-connect coupler and an electrical socket, respectively.

The electrical unit 146 is electrically connected to the wire 118. The electrical unit 146 controls the flow of electrical power to the tip 108 to operate the device 100 in one of its operating modes through actuation of the aforementioned buttons 114, 116.

Figure 2:
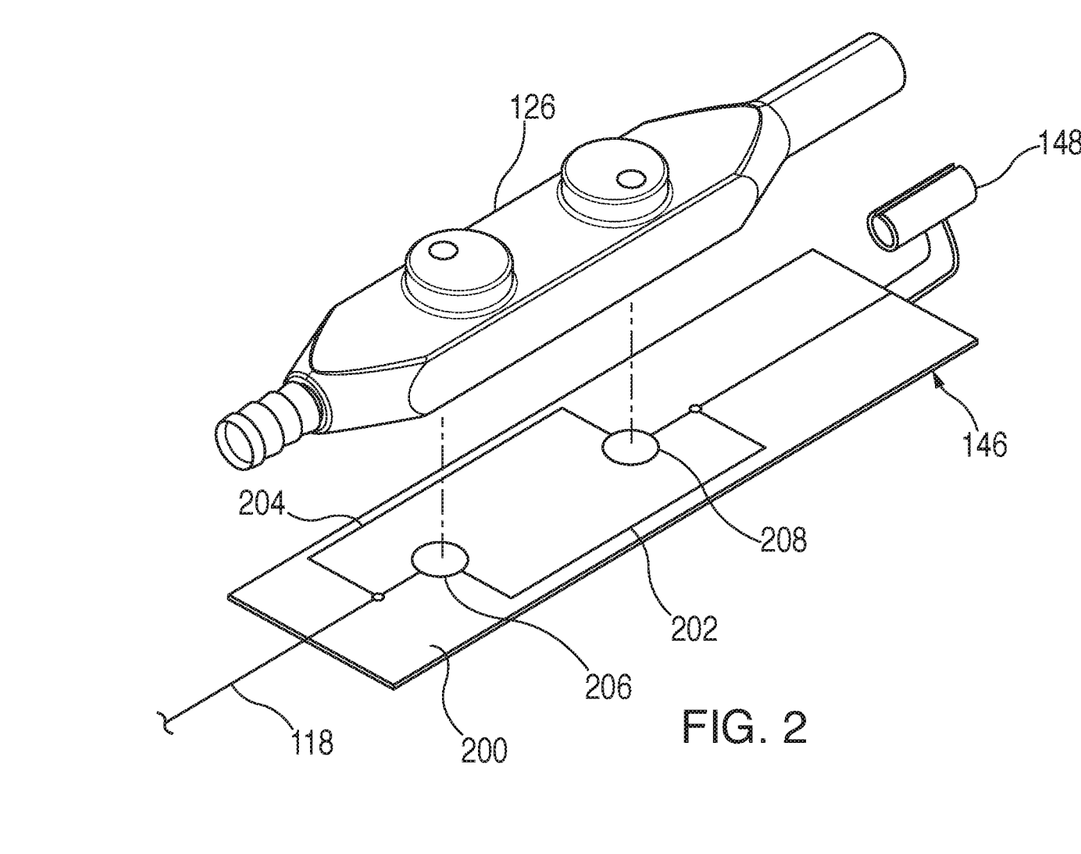
FIG. 2 is an assembly drawing of a valve train and an electrical unit of the cautery device shown in FIGS. 1a and 1b.

As shown in FIG. 2, in one embodiment, the electrical unit 146 may be constructed as a printed circuit board 200 having a plurality of circuits 202, 204 from the power source to the electric coupler 148. Each of the circuits 202, 204 may correspond to a respective one of the buttons 114, 116 and, therefore, to a mode of operation of the device 100. Specifically, circuit 202 includes a first switch 206 that may be actuated by the first button 114 and circuit 204 includes a second switch 208 that may be actuated by the second button 116. Each circuit 202, 204 may be constructed to regulate the power level delivered to the cautery tip 108 when the respective switches 206, 208 are actuated. For example, a first circuit 202 may be activated by the first switch 206 to energize the tip 108 so that it can cut tissue (e.g., a cutting mode), while the second circuit 204 may be activated by the second switch 208 to energize the tip 108 so that it can coagulate fluid (e.g., a coagulation mode).

By way of example, in one embodiment, button 114 may be used to operate the device 100 in a cutting mode and button 116 may be used to operate the device 100 in a coagulation mode. A surgeon may press button 114 to simultaneously open the first valve 138 to allow for the gas to flow at a first flow rate to the tip assembly 142 and to energize the first circuit 202 to supply electrical energy to the tip 108 sufficient for operating the device 100 in a cutting mode. Similarly, a surgeon may press the second button 116 to open the second valve 140 to allow for a second gas flow rate to the tip assembly 142 and to simultaneously energize the second circuit 204 to supply electrical energy to the tip 108 sufficient for operating the device 100 in a coagulation mode. The first and second flow rates may be the same or different based on the operating mode selected by pressing the associated buttons 114, 116. The first and second flow rates are sufficient to supply the gas at least in a quantity to the open end of the tip 108 to create a zone about the tip which is not flammable when the device is operated in any of its operating modes, e.g., coagulation or cutting. Also, each of the first and second flow rates may be variable based on the range of motion (distance the button is depressed) of the switch button.

In one embodiment, the flow of gas and electricity to the cautery tip 108 may be interlocked together so that a flow of gas is initiated only when the tip 108 is energized in one of its operating modes (e.g. cutting or coagulation). Also, in another embodiment, the flow of gas may be initiated without (independently of) energizing the tip 108. For example, the buttons 114 and/or 116 may have a range of motion in which an initial range of motion (i.e., of button depression) of the button may only permit gas to flow and a secondary range of motion (i.e., further button depression) of the button may cause both gas and electricity to flow to the tip. The flow of gas and electricity may thus occur together or without electricity (i.e., gas only).

Figures 3, 4:
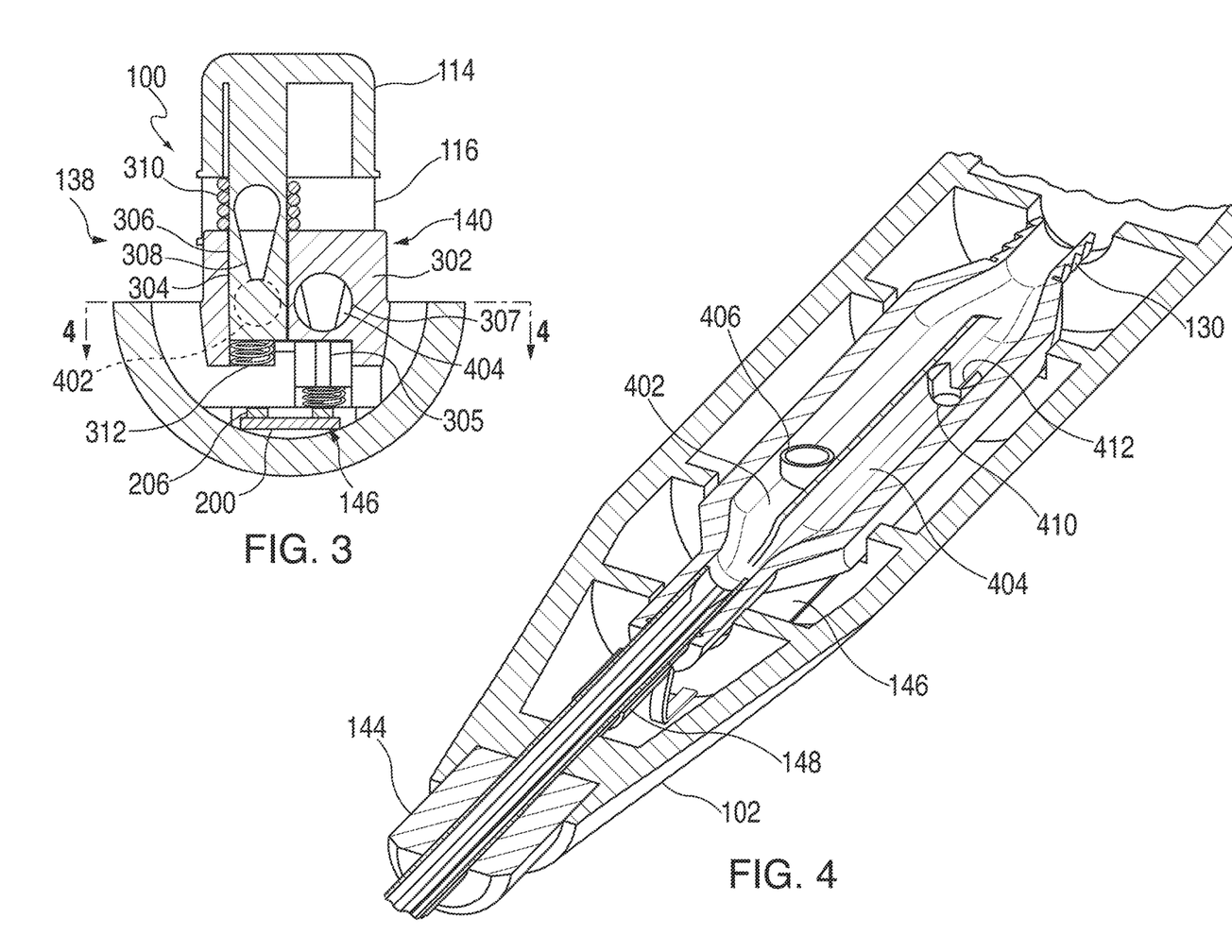

The construction of the valve train and the operation of the gas and electricity flow will now be described in greater detail. FIG. 3 shows cutaway section views of the valve train 126 shown in FIG. 1B.

FIG. 3 shows a section view of the device 100 along section 3-3 in FIG. 1A. As shown in FIG. 3, the valves 138 and 140 are arranged as gate valves. The construction of valve 138 will now be described. It will be appreciated that the construction of valve 140 may be the same, although dimensions may be different. Valve 138 has a valve body 302 that is disposed in the first channel 402 (FIG. 4) of the valve train 126. Valve 138 has a valve stem 304 that is received in a vertical bore 306 of the body 302 that intersects with the first channel 402 (FIG. 4). The valve stem 304 has a teardrop shaped port 308 formed therein, which is tapered towards the bottom of the valve stem 304 and is enlarged toward the top of the valve stem 304. The valve stem 304 is coupled to the first button 114. A coil spring 310 is interposed between the button 114 and the body 302 to bias the valve stem 304 in an upward, closed position in which the port 308 is not in communication with the first channel 402, as is shown in FIG. 3. When the valve stem 304 is positioned as shown in FIG. 3, the stem 304 is seated in the housing and fully blocks the port 308 to maintain the valve 138 in a closed position. The valve stem 304 is constructed to move vertically in the vertical bore 306 so as to progressively open and close the flow of gas through the port 308 and the first gas channel 402.

The electrical unit 146 is shown below the valve train 126. The first switch 206 is aligned with the valve stem 304. A first coil spring 312 extends upward from the first switch 206. When the first valve 138 is in the fully closed position, the spring is spaced from the bottom of the valve stem 304. The first switch 206 may be constructed to actuate in response to compression of the first coil spring 312.

The valve stem 304 may be moved downward from the closed position by pushing on the button 114 against the force of the spring 310. As the valve stem 304 moves downward, the bottom of the port 308 will begin to come into fluid communication with the first gas channel 402, creating a relatively small opening for gas to flow between the port 308 and the first channel 402. Also, as the bottom of the valve stem 304 moves downward it begins to compress the first coil spring 312, which causes the first switch 206 to actuate (i.e., to close the first circuit 202), permitting power to flow through the first circuit 202 to the cautery tip 108 at a power level regulated by the first circuit 202 and corresponding to a first operation mode.

As the valve stem 304 is moved progressively further downward, the port 308 is progressively moved further downward enlarging the opening between the port 308 and the first channel 402 until the top of the port 308 is aligned with the top of the channel 402, in which case the valve 138 is considered to be in a fully open position. The further movement of the valve stem 304, however, does not change the state of the first circuit 202, which remains energized owing to the further compression of the first coil spring 312. Thus, in view of the foregoing description it will be appreciated by one of skill in the art that in at least one embodiment of the cautery device 100 a user can regulate the flow rate of gas through the valve train 126 and the cautery tip 108 by adjusting the travel distance of the button 114. Such flow regulation may be useful for a surgeon to adjust the flow rates around tissue vessels of different sizes. For example, for blowing gas around small vessels, a user may desire only a relatively small wisp of gas, while for blowing gas around larger vessels, a user may desire a relatively larger flow to displace fluid from the area.

FIG. 4 shows a detailed section view of the device 100 across section 4-4 in FIG. 3. The valve train 126 defines the first gas channel 402 in which the stem 304 of the first valve 138 is received and a second gas channel 404 in which a second valve stem 305 (FIG. 3) of the second valve 140 is received. The first and second channels 402, 404 both extend from the proximal end 128 to the distal end 132 of the valve train 126. The first gas channel 402 has a first opening 406 that is aligned with the first bore 306 of the first valve 138. The first opening 406 receives the first valve stem 304. The second gas channel 404 has a second opening 410 that is aligned with a second bore 307 (FIG. 3) of the second valve 140. The second opening 410 receives the second valve stem 305 (FIG. 3) of the second valve 140. The first valve stem 304 is constructed to move vertically in the opening 406 to actuate the first switch 206 of the first circuit 202 of the electrical unit 146, which is below the valve train 126. Similarly, the second valve stem 305 is constructed to move vertically in the opening 410 to actuate the second switch 208 of the second circuit 204 of the electrical unit 146. The first and second valves 138, 140 may be of the same construction or may be different.

In one embodiment of the device 100, the first and second buttons 114, 116 may be pressed independently of one another and both can be pressed partially between the open and closed valve positions. However, the cautery tip 108 may be configured to operate in only a single operating mode, such as cutting or coagulating. For example, in one embodiment the electrical unit 146 may be constructed to ignore the actuation of all pressure switches (e.g., 206, 208) other than the switch that is actuated first in time. In another embodiment, however, the electronic unit 146 may be constructed to ignore the actuation of all pressure switches (e.g., 206, 208) other than the switch that sets the highest power output to the cautery tip 108. In any event, it will be appreciated based on the foregoing disclosure that the independent opening of multiple valves (e.g., 138, 140) will increase the gas flow rate issuing from the cautery tip 108 relative to if only a single valve was opened. Alternatively, in one embodiment, instead of independent operation of buttons 114, 116, the two buttons 114, 116 shown in FIG. 1B may be covered by a cover and connected together with a rocker arm (not shown) so that only one button (114 or 116) may be depressed at a time.

Figures 5A, 5B:
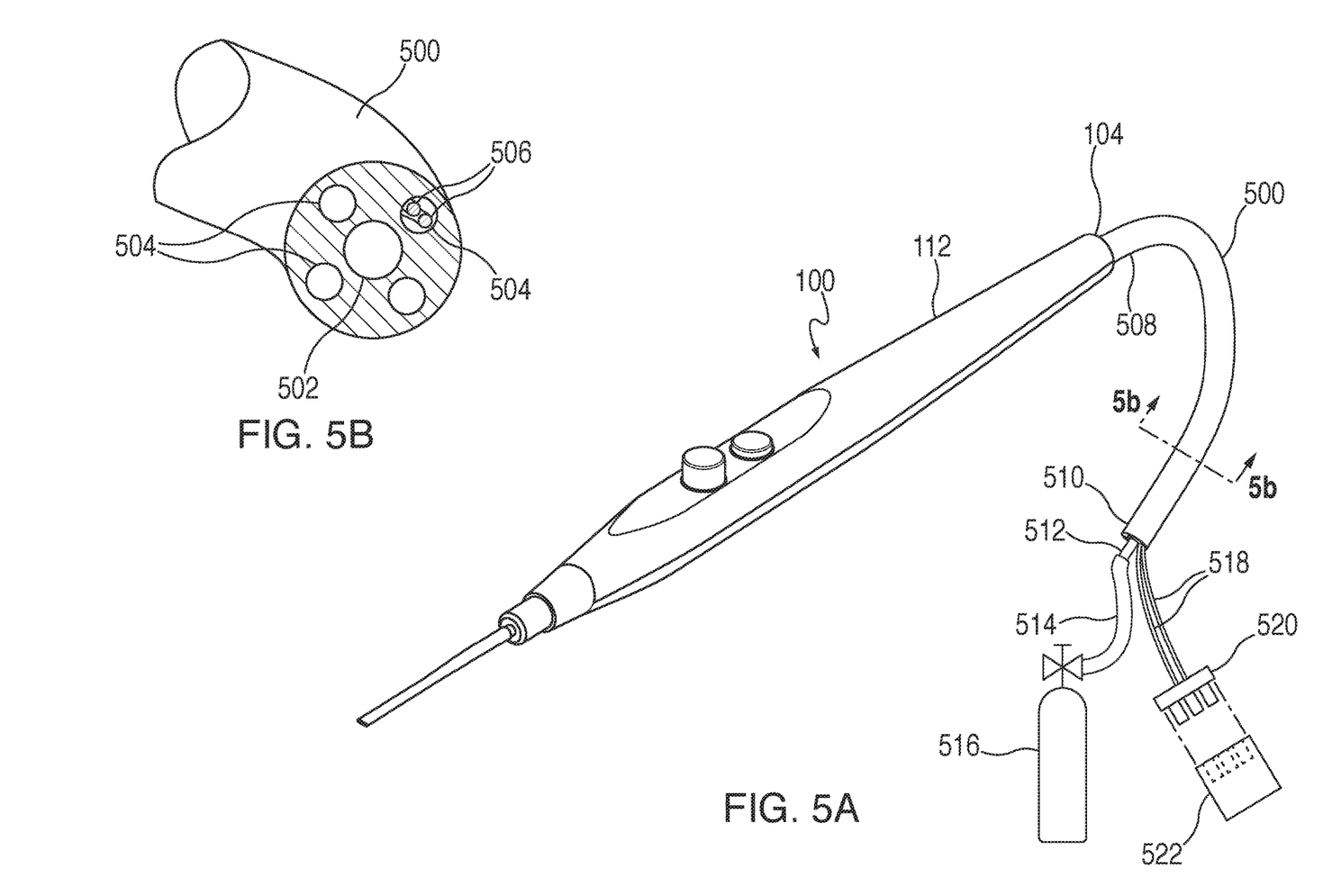
Figure 6:
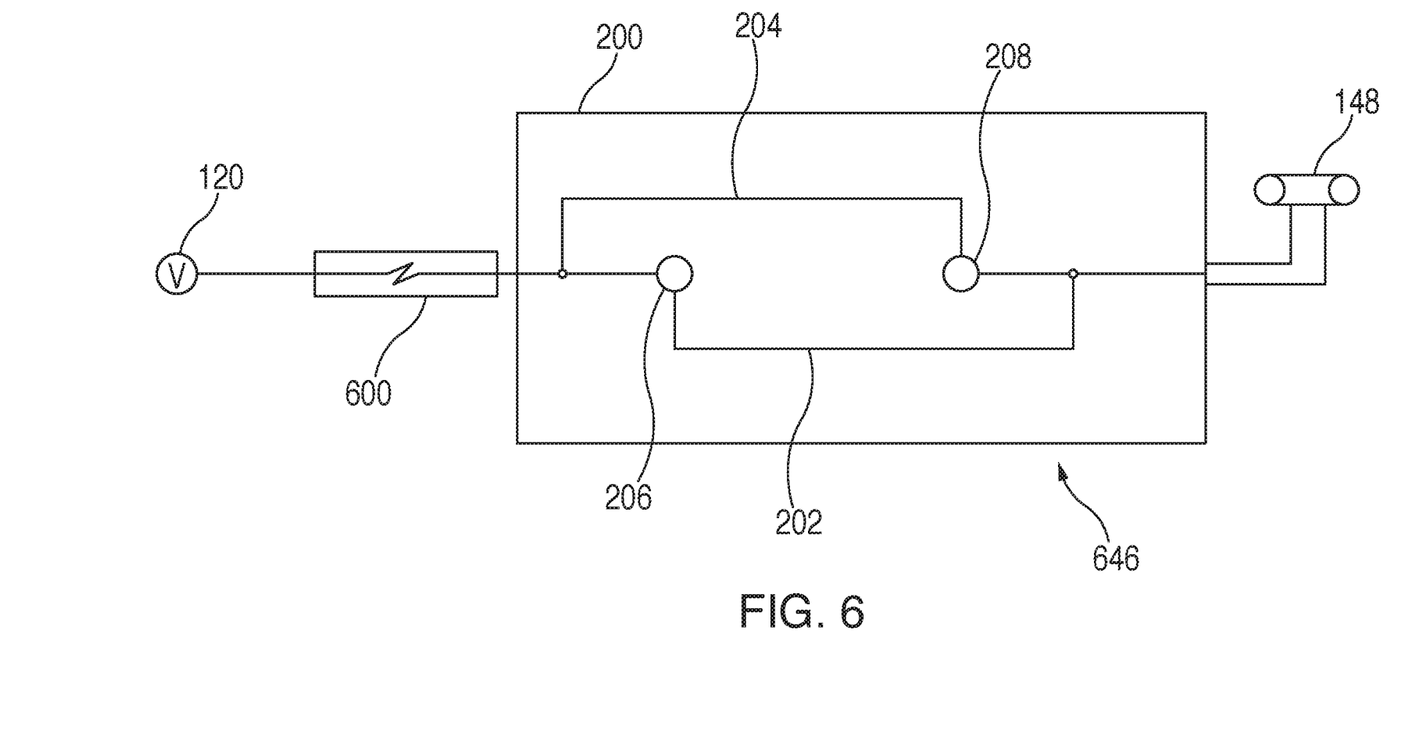
FIG. 6 is a schematic view of the electrical unit of FIG. 2, shown connected to a magnetic reed switch.

In a further aspect, the tube 122 and electrical wire 118 extending from the handpiece 112 in FIG. 1a may be integrally formed into a multilumen tubing 500, as show for example in FIGS. 5 and 6. The multi-lumen tubing 500 defines a central lumen 502 for carrying the gas, and defines circumferentially spaced lumens 504 around the central lumen 502 for carrying electrical conductors 506. The electrical conductors 506 may be bare conductors or may be insulated inside the lumens 504. The tubing 500 is preferably constructed of an electrically insulated material. The tubing 500 may extend from a first end 508, at the proximal end 104 of the housing 102 of the device 100, to a second end 510 proximal of the first end 508. The second end 510 of the tubing 500 may have terminations to connect to the fluid and electrical power supplies 516 and 522. In one embodiment, a push-on barbed fitting 512 is inserted into the central lumen 502 and the barbed fitting 512 is connected to a tube 514 for fluid coupling to a supply of gas 516. Also, in one embodiment, the conductors 518 extend beyond the second end 510 of the multilumen tubing 500 a certain distance and terminate in an electrical connector 520, such as a three prong plug, for electrical coupling to a mating electrical receptacle 522.

In yet another aspect, the device 100 may include a safety switch 600 (FIG. 6) that may be electrically connected in series with the electrical unit 146 to cut off power to the cautery tip 108 when the device 100 is disposed in a designated holder 700 (FIG. 7) that is constructed to hold the device 100 when it is not in use (i.e., not being actively handled by a user). In one embodiment, a magnetic reed switch 600 is coupled between the electrical unit 146 and the electrical supply 120. The magnetic reed switch 600 may be a normally closed switch that will normally energize the electrical unit 146 when it is not in the presence of a magnetic field.

Figure 7:
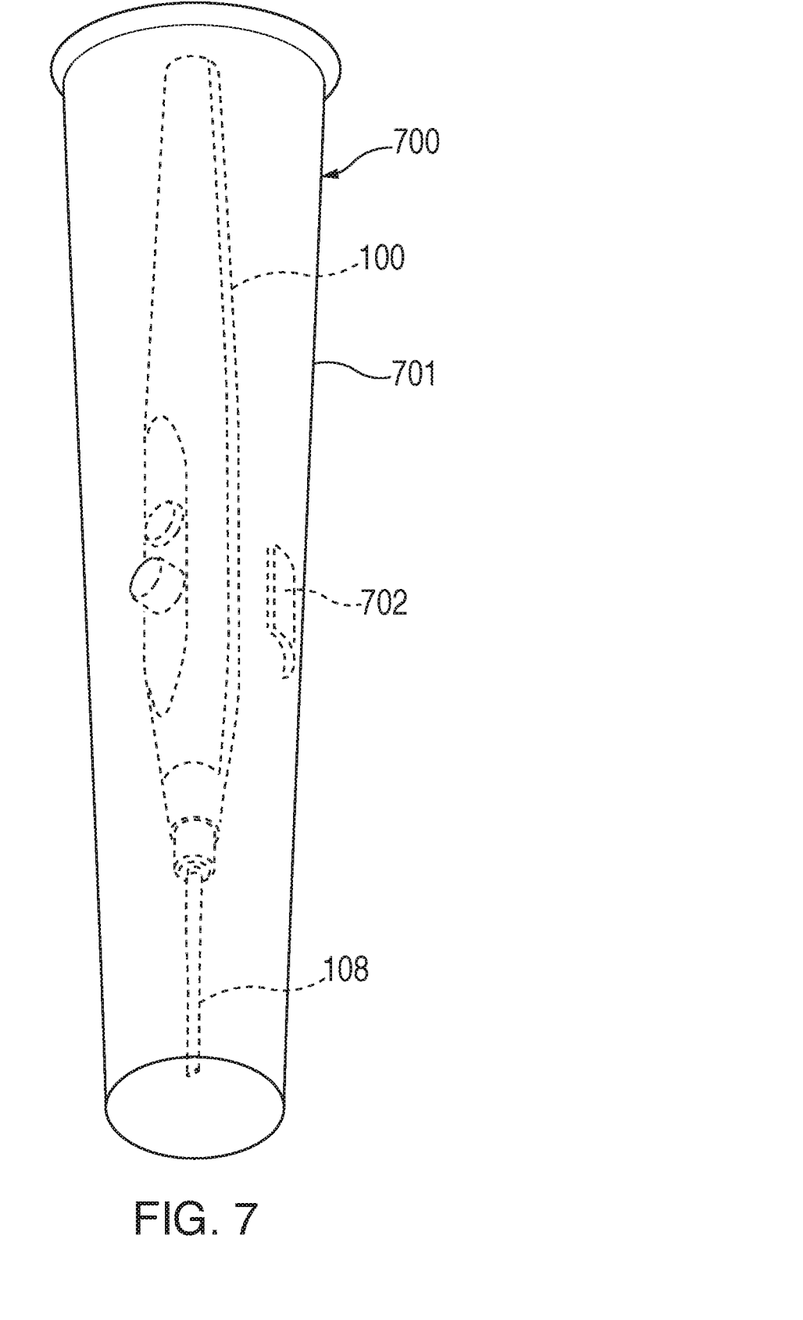
FIG. 7 shows a cautery device disposed in a holder.

The holder 700 may include an elongated, open receptacle 701, shown in FIG. 7, which can receive the device 100. Also, the holder 700 may include a permanent magnet 702 mounted to the receptacle 701 so that a magnetic field may be generated by the magnet 702 inside the receptacle 701. Preferably, the permanent magnet 702 is mounted at a position inside the receptacle 701, such that the magnetic field will open the reed switch 600 when the device 100 is disposed in the receptacle 701. In one embodiment, the cautery device 100 is disposed vertically or at a downward angle within the receptacle 701 with the tip 108 pointed down towards a bottom of the receptacle 701. The magnet 702 is positioned in the receptacle 701 so that the magnet 702 is at or near the location of the reed switch 600 when the device 100 is disposed in the receptacle 701 with the tip 108 pointed down. When the device 100 is placed inside the receptacle 701, the magnetic field generated by the magnet 702 will open the reed switch 600 and prevent closure of the activating circuits. Thus, when the device 100 is disposed in the holder, the cautery tip 108 cannot receive power and cannot heat up, which may prevent accidental fires.

Figure 8:
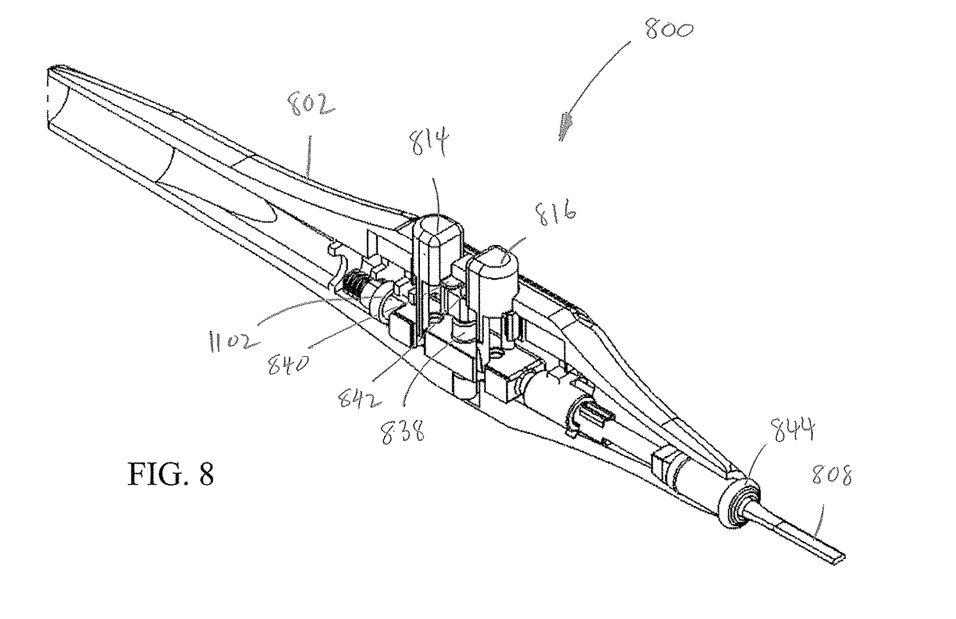
FIG. 8 is a perspective partial section of another embodiment of a cautery device.
Figure 9:
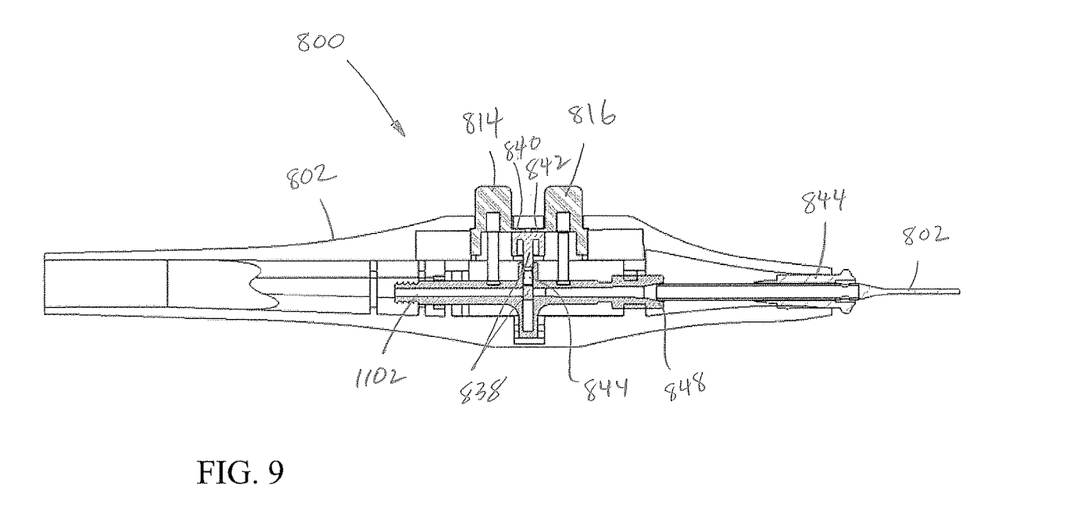
FIG. 9 is a longitudinal section of the cautery device of FIG. 8.

Turning now to FIGS. 8 and 9, another embodiment of a cautery device 800, substantially similar to cautery device 100 (with like parts having reference numerals incremented by 700 relative thereto), is shown. Cautery device 800 includes an electrical unit (not shown, but similar to electrical unit 146 in FIG. 6) and two buttons 814, 816 in the handpiece 802 that are adapted to actuate the electrical unit in a cautery energy mode or a coagulation energy mode to appropriately provide energy to a cautery tip 808 received in a socket in the distal end of the handpiece 802.

In accord with one aspect of cautery device 800, the handle includes a single gas channel 1102. The two buttons 814, 816 for actuating modes of the electrical unit are each coupled to one common valve 838. The valve 838 controls the flow of gas across the gas channel 1102. The buttons have a range of motions, and when either of the buttons is depressed, an opening 844 in the valve 838 is displaced toward an open position to permit a controlled fluid flow through the gas channel 1102 and toward the distal end of the handle. Preferably, the valve 838 has a range of motion and is progressively opened by as a function of a distance traveled the depressed button. Moreover, it is preferred that when a first pressure is applied to the buttons 814, 816, the valve 838 is at least partially opened to allow passage of the gas prior to initiating actuation of the electrical unit 146, which occurs upon applying a second higher pressure. In accord with one construct, the buttons 814, 816 are each provided with a flange 840, 842 that contacts an upper end of the valve 838. Depression of the individual buttons 814, 816 results in corresponding movement of the valve 838. The valve 838 will be displaced by the maximum amount of movement of either of the buttons 814, 816, with maximum displacement of the valve 838 preferably resulting in maximum gas flow through the gas channel 1102.

Figure 10:
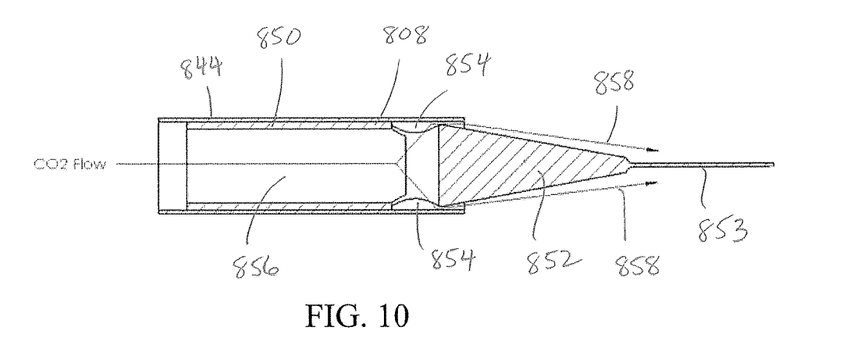
FIG. 10 is an enlarged longitudinal section of the distal end of the cautery device of FIG. 8, showing a replaceable tip.

Referring now to FIGS. 9 and 10, the cautery tip 808 is received in the socket 848 and is stabilized by a distal collet 844. The cautery tip 808, and has a proximal portion 850 and a distal end 852. In accord with another aspect of the embodiment, the cautery tip 808 has a hollow proximal portion 850 integrated and unitary with the solid (or closed-end) distal portion 852 tapering to a distal tip 853. The hollow portion 850, via the socket 848, is in fluid communication with the gas channel 1102 and defines a gas passage in at least the proximal portion of the cautery tip. The gas passage 856 in the cautery tip is preferably coaxial with the gas channel. The cautery tip 808 includes a plurality of circumferentially-displaced and preferably radially-oriented holes 854 therein, between the hollow proximal 850 and solid distal portion 852 of the cautery tip. The holes 854 allow the gas flowing through the hollow portion to exit the cautery tip and pass out of the handle and circumferentially about the distal portion 852, as indicated by arrows 858.

Figure 11:
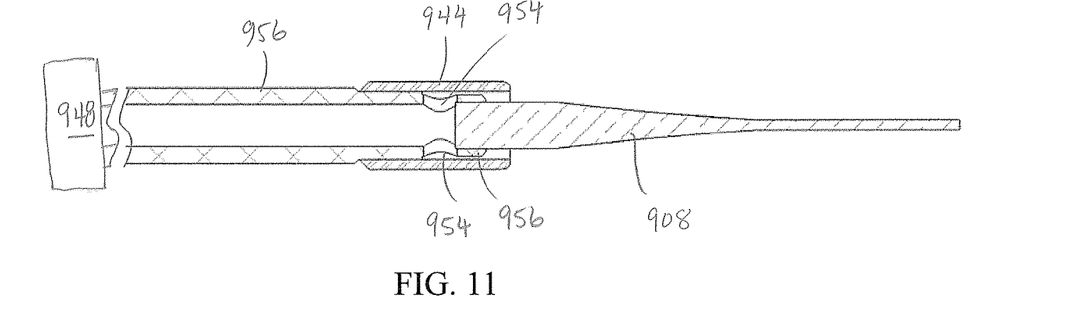
FIG. 11 is a view similar to FIG. 10, showing another replaceable tip.

Turning now to FIG. 11, another embodiment of a removably coupled cautery tip 908 is shown electrically coupled to an electrical coupler 948 of a handpiece of the cautery device. An extension tube 956 extends from the electrical coupler 948 and has a distal end stabilized within a distal collet 944 of the handpiece. The extension tube 956 is provided with a plurality of circumferentially-displaced and preferably radially-oriented holes 954, and a distal mount 956 for receiving a removable cautery tip 908. The removable cautery tip 908 is a solid structure, tapering in dimension as it extends distally away from the handpiece. The extension tube 956 is in fluid communication with the gas channel 1102 of the handpiece 802 (FIG. 9). When the gas valve 838 is opened, gas flows through the extension tube 956, preferably coaxially with the gas channel, then radially out of the circumferential holes 954, and into the collet 944. The extension tube 956 fills the proximal end of the collet 944. As a result, the gas then exits distally through the collet and then circumferentially about the solid cautery tip 908. The solid cautery tip 908 may be removably interference fit within the distal end of the extension tube 956 and replaced with a different tip, particularly a tip having a different shape.

Turning back to FIGS. 1A, 1B and 2, in one embodiment of the device 100, the first and second buttons 114, 116 may be pressed independently of one another and both can be pressed partially between the open and closed valve positions. However, the cautery tip 108 may be configured to operate in only a single operating mode, such as cutting or coagulating. For example, in one embodiment the electrical unit 146 may be constructed to ignore the actuation of all pressure switches (e.g., 206, 208) other than the switch that is actuated first in time. In another embodiment, however, the electronic unit 146 may be constructed to ignore the actuation of all pressure switches (e.g., 206, 208) other than the switch that sets the highest power output to the cautery tip 108. In any event, it will be appreciated based on the foregoing disclosure that the independent opening of multiple valves (e.g., 138, 140) will increase the gas flow rate issuing from the cautery tip 108 relative to if only a single valve was opened. Alternatively, in one embodiment, instead of independent operation of buttons 114, 116, the two buttons 114, 116 shown in FIG. 1B may be covered by a cover and connected together with a rocker arm (not shown) so that only one button (114 or 116) may be depressed at a time. Any and all of these features may similarly be incorporated into cautery device 800.

There have been described and illustrated herein several embodiments of a cautery device. While particular embodiments of the invention have been described, it is not intended that the invention be limited thereto, as it is intended that the invention be as broad in scope as the art will allow and that the specification be read likewise. Thus, while particular button and cautery tip arrangements have been disclosed, it will be appreciated that other button and tip arrangements may be employed as well. In addition, while a particular type of safety switch has been disclosed, it will be understood that other switches having the same or similar functionality can be used. For example, and not by way of limitation, GMR (Giant Magneto Resistive), AMR (Anisotropic Magneto Resistive), and Hall Effect switches may be used. Also, while a particular multi-lumen geometry has been disclosed, other geometries are possible. Also, while carbon dioxide may be preferred as an inert gas, it will be recognized that other gases that are non-flammable may be used. Also, while several cautery tips have been shown including gas flow passages through at least a portion of the tip, it is recognized that other configurations suitable for the purposes herein can be used. Moreover, the features of the several embodiments described herein can be used together (mixed and matched), without limitation. It will therefore be appreciated by those skilled in the art that yet other modifications could be made to the provided invention without deviating from its scope as claimed.

What is claimed is:

1. A cautery system, comprising:
an elongated handpiece extending axially from a proximal end to a distal end;
a cautery tip extending from the distal end of the handpiece;
a gas supply connection extending from the handpiece for supplying gas at the cautery tip;
a gas source connected to the gas supply connection which supplies non-flammable gas for delivery to the cautery tip;
an electric supply connection extending from the handpiece for connection to an electric supply for delivering energy to the cautery tip, the electric supply connection electrically coupled to the cautery tip;
an electrical unit configured to control the delivery of energy to the cautery tip from the electric supply, wherein when energy is delivered to the cautery tip from the electric supply the cautery tip is adapted to at least one of cut or coagulate tissue;
a spring disposed in direct contact with the electrical unit at least one button coupled to the handpiece that actuates the electrical unit for selectively delivering energy to the cautery tip; and
a single valve fluidly coupled between the cautery tip and the gas supply connection, the valve adapted to regulate a variable flow rate of the non-flammable gas from the gas supply connection to the cautery tip, the valve coupled to the at least one button such that when the at least one button is actuated, the valve moves within the handpiece from a closed configuration toward an open configuration to actuate the electrical unit to control the delivery of energy to the cautery tip and to permit the delivery of the non-flammable gas to the cautery tip, the at least one button configured to maintain the delivery of the energy to the cautery tip while adjusting the delivery of the non-flammable gas to the cautery tip by causing the valve, while in the open configuration, to compress the spring against the electrical unit while the valve is moving within the handpiece.

2. The cautery system according to claim 1, wherein the non-flammable gas is carbon dioxide and creates a non-flammable zone around the cautery tip.

3. The cautery system according to claim 1, wherein:
the at least one button includes a first button and a second button,
the first button, when pressed, actuating the electrical unit to deliver energy to the cautery tip suitable for coagulating tissue, and
the second button, when pressed, actuating the electrical unit to deliver energy to the cautery tip suitable for cauterizing tissue.

4. The cautery system according to claim 1, wherein the valve has a range of motion and is progressively opened as a function of a distance traveled by the at least one button.

5. The cautery system according to claim 1, wherein the at least one button has a range of motion, and the flow rate of the non-flammable gas is adjustable based on the position of the at least one button in the range of motion.

6. The cautery system according to claim 1, wherein a first pressure applied to the at least one button at least partially moves the valve to the open configuration to permit the delivery of non-flammable gas to the cautery tip without actuation of the electrical unit, and a second pressure greater than the first pressure applied to the at least one button actuates the electrical unit.

7. The cautery system according to claim 1, wherein the electrical unit is removably coupled to the cautery tip.

8. The cautery system according to claim 1, wherein the cautery tip is replaceable within the handpiece.

9. The cautery system according to claim 1, wherein the electrical unit has a plurality of circuits, each circuit supplying a predetermined amount of energy for delivery to the cautery tip based on actuation of the at least one button.

10. The cautery system according to claim 1, wherein the gas supply and the electric supply are coupled to the handpiece through a multilumen flexible tube, and the gas supply and electric supply are coupled to the handpiece through respective lumens of the multilumen flexible tube.

11. The cautery system of claim 1, further comprising:
a holder adapted to receive the handpiece; and
a switch coupled to the handpiece configured to control the delivery of energy to the cautery tip based on a position of the handpiece relative to the holder.

12. The cautery system of claim 11, wherein the switch is a normally closed switch that is configured to permit the delivery of energy to the cautery tip when the handpiece is not disposed in the holder and is configured to prevent the delivery of energy to the cautery tip when the handpiece is disposed in the holder.

13. A cautery system, comprising:
a handpiece, a gas lumen extending through the handpiece and an electrical unit provided within the handpiece, the electrical unit having a control circuit and a socket;
a cautery tip removably electrically coupled within the socket and extending distally from the handpiece, the cautery tip having a proximal portion, a distal end, and a hollow gas passage defined in at least the proximal portion of the cautery tip, wherein the electrical unit is configured to deliver energy to the cautery tip to at least one of cut or coagulate tissue;
a gas supply connection configured to deliver non-flammable gas to the gas lumen, the gas lumen in fluid communication with the hollow gas passage of the cautery tip so that the non-flammable gas delivered via the gas supply connection can flow through the hollow gas passage of the cautery tip and toward the distal end of the cautery tip to create a non-flammable zone around the cautery tip; and a collet defining a longitudinal lumen configured to removably receive a portion of the cautery tip for stabilizing the cautery tip within the handpiece, the portion of the cautery tip removably received within the collet having an outer surface that defines a plurality of radial openings in fluid communication with the hollow gas passage of the cautery tip such that the non-flammable gas flowing through the hollow gas passage exits the cautery tip into the longitudinal lumen defined by the collet via the plurality of radial openings.

14. The cautery system of claim 13, wherein the handpiece extends axially from a proximal end to a distal end of the handpiece, and the socket is disposed at the distal end of the handpiece.

15. The cautery system of claim 13, wherein the gas passage of the cautery tip and at least a portion of the gas lumen are coaxial.

16. The cautery system of claim 13, wherein the cautery tip has a closed distal end.

17. The cautery system of claim 16, wherein the distal end of the cautery tip tapers to a smaller dimension.

18. The cautery system of claim 13, further comprising:
a holder adapted to receive the handpiece; and
a switch coupled to the hand piece and configured to control the delivery of energy to the cautery tip based on a position of the handpiece relative to the holder.

19. The cautery system of claim 18, wherein the switch is a normally closed switch that is configured to permit the delivery of energy to the cautery tip when the handpiece is not disposed in the holder and is configured to prevent the delivery of energy to the cautery tip when the handpiece is disposed in the holder.

20. A cautery system, comprising:
an elongated handpiece;
a cautery tip extending distally from the handpiece;
an electrical unit configured to control delivery of energy to the cautery tip for treating tissue;
a spring disposed in direct contact with the electrical unit at least one button coupled to the handpiece and configured to actuate the electrical unit for delivering electrical energy to the cautery tip; and
a valve configured to control delivery of a gas from a gas source to the cautery tip, the valve coupled to the at least one button such that when the at least one button is actuated, the valve moves within the handpiece from a closed configuration toward an open configuration to actuate the electrical unit to control delivery of energy to the cautery tip and to permit delivery of the gas to the cautery tip, the at least one button configured to maintain the delivery of energy to the cautery tip while adjusting the delivery of the non-flammable gas to the cautery tip by causing the valve, while in the open configuration, to compress the spring against the electrical unit while the valve is moving within the handpiece.

* * * * *